United States Patent
McDermott et al.

(10) Patent No.: US 7,231,257 B2
(45) Date of Patent: Jun. 12, 2007

(54) COCHLEAR IMPLANT SOUND PROCESSING METHOD AND SYSTEM

(75) Inventors: Hugh McDermott, Mt. Macedon (AU); Colette McKay, East Melbourne (AU)

(73) Assignee: The University of Melbourne, Parkville, Victoria (AU)

( * ) Notice: Subject to any disclaimer, the term of this patent is extended or adjusted under 35 U.S.C. 154(b) by 396 days.

(21) Appl. No.: 10/787,260

(22) Filed: Feb. 27, 2004

(65) Prior Publication Data
US 2005/0107843 A1    May 19, 2005

(30) Foreign Application Priority Data
Feb. 28, 2003   (AU) .............................. 2003901025

(51) Int. Cl.
*A61N 1/00*    (2006.01)
(52) U.S. Cl. ...................................... 607/57
(58) Field of Classification Search ............ 607/55–57
See application file for complete search history.

(56) References Cited

FOREIGN PATENT DOCUMENTS

WO    WO 91/05523    5/1991

OTHER PUBLICATIONS

Carlyon, R.P, "Detecting pitch-pulse asynchronies and differences in fundamental frequency." *Journal Of Acoustical Society of America* 95(2): 968-79 (1994).

Carlyon, R.P, et al., "Comparing the Fundamental Frequencies of Resolved and Unresolved Harmonies—Evidence for Two Pitch Mechanisms", *Journal Of Acoustical Society of America* 96(6): 3541-3554 (1994).

Carlyon, R.P, et al., "Temporal pitch mechanisms in acoustic and electric hearing", *Journal Of Acoustical Society of America* 112(2): 621-33 (2002).

Culling, et al. "Perceptual separation of concurrent speech sounds: absence of across-frequency grouping by common interaural delay", *Journal Of Acoustical Society of America* 98(2Pt. 1): 785-97 (1995).

Durlach, et al. "Interaural correlation discrimination: II. Relation to binaural unmasking", *Journal Of Acoustical Society of America* 79(5): 1548-57 (1986).

Gabriel, et al. "Interaural correlation discrimination: i. bandwidth and level dependence", *Journal Of Acoustical Society of America* 69(5): 1394-401 (1981).

McKay et al. "The perception of temporal patterns for electrical stimulation presented at one or two intracochlear sites", *Journal Of Acoustical Society of America* 100(2Pt.1): 1081-92 (1996).

Plack, et al., "Pitch matches between unresolved complex tones differing by a single interpulse interval", *Journal Of Acoustical Society of America* 108(2): 696-705 (2000).

(Continued)

*Primary Examiner*—Scott M. Getzow
(74) *Attorney, Agent, or Firm*—McDermott Will & Emery LLP (57) ABSTRACT

An auditory prosthesis device for selectively stimulating electrodes within an auditory prosthesis electrode array, comprising a transducer (2) for converting a complex acoustic sound into an electrical signal; signal processing means (13) responsive to an electrical signal and generating a temporal pattern of stimulation pulses to selected electrodes within the electrode array, the stimulation pulses being applied to each electrode at an electrode stimulation rate; feature extraction means (14) for deriving an estimate of at least one fundamental frequency of the electrical signal; and stimulation pulse adjustment means (15) for adjusting the stimulation pulses in accordance with the estimated fundamental frequency.

38 Claims, 4 Drawing Sheets

OTHER PUBLICATIONS

Shamma, et al., "The case of the missing pitch templates: how harmonic templates emerge in the early auditory system", *Journal Of Acoustical Society of America* 107(5Pt.1): 2631-44 (2000).

Vliegen, et al., "The role of spectral and periodicity cues in auditory stream segregation, measured using a temporal discrimination task", *Journal Of Acoustical Society of America* 106(2): 938-45 (1999).

COCHLEAR IMPLANT SOUND PROCESSING METHOD AND SYSTEM

The present invention relates generally to the generation of electrical stimuli for application to an auditory prosthesis electrode array forming part of a cochlear implant.

Cochlear implants are now the clinical device of choice for people who have a profound hearing loss. Such implants typically consist of an internal and an external component. The internal component consists of an array of electrodes implanted within the cochlea, and associated electronics for providing current stimulation to the surviving auditory neural elements. The external device is a sound processor, which converts an incoming acoustic signal into appropriate electrical stimulation pulses for application to the electrode array.

Cochlear implant technology has progressed to the stage that the average user can expect to understand conversational speech in quiet surroundings without the aid of lip reading. However, cochlear implants do not provide a satisfactory hearing experience when listening to speech in the presence of other noises, and when listening to musical sounds and in particular when listening to melody. There are thought to be two principle reasons for this: firstly, the pitch of complex sounds, generally related to the fundamental frequency, is poorly conveyed by current speech processing schemes, and secondly, the fine temporal and spectral information that normally hearing people use to segregate a complex sound from noise or other complex sounds is lost or reduced in implant processing.

Fine temporal information in acoustic sounds is represented by relatively fast amplitude fluctuations in the wave form of the signal. For periodic (or harmonic) complex signals, such as voiced speech or musical sounds, the fundamental frequency (F0) is related to the period of fluctuation, and leads to the perception of musical pitch or voice pitch. The fundamental frequency of these sounds generally lies between 50 Hz and at least several hundred Hz. Finer temporal information is provided by the frequencies of the harmonic components of such sounds, which are at multiples of the fundamental frequency.

The signal processing applied in current cochlear implant sound processors does not allow the fine frequency perception that this would require, either spectrally or temporally. In the spectral dimension, up to about twenty fixed narrow band filters are usually assigned tonotopically to the electrode positions in the cochlea. This arrangement does not allow the implantee to resolve harmonic components of complex sounds, and hence to perceive the fundamental frequency via the spectral template method. In the temporal domain, the output of the filters will have amplitude modulations at the fundamental frequency rate, provided that the filters are wide enough to encompass more that one harmonic, and provided that smoothing functions at the output of the filters do not attenuate this modulation. In theory, these modulations could provide a fundamental frequency pitch perception, provided that the rate of stimulation is high enough to accurately "sample" this modulation pattern.

However, recent studies have shown that users of one of the most common processing strategies used in cochlear implants, namely the Spectral Peak or SPEAK strategy, could not discriminate the pitch of some complex sounds. Inspection of the processor output showed amplitude modulations for low fundamental frequencies, but the modulations on different electrodes appear to have somewhat random phase relationships. It has also been shown that phase shifts on nearby electrodes will impair the ability of the implantee to perceive the modulation frequency, or cause them to perceive a pitch not related to the fundamental frequency.

It would therefore be desirable to provide a cochlear implant sound processing strategy to improve the perception of fundamental frequency for speech and musical stimuli.

It would also be desirable to provide a cochlear implant sound processing strategy to allow the important components of a complex sound, such as a vowel sound or a musical note, to be perceptually grouped by an implantee.

It would also be desirable to provide a cochlear implant sound processing strategy to allow two or more concurrent complex sounds, such as two speakers, to be better perceptually segregated by an implantee.

It would also be desirable to provide a cochlear implant sound processing strategy that ameliorates or overcomes one or more disadvantages of the prior art.

With this in mind, one aspect of the present invention provides an auditory prosthesis device for selectively stimulating electrodes within an auditory prosthesis electrode array, comprising:

a transducer for converting a complex acoustic sound into an electrical signal, signal processing means responsive to an electrical signal and generating a temporal pattern of stimulation pulses to selected electrodes within the electrode array, the stimulation pulses being applied to each electrode at an electrode stimulation rate, feature extraction means for deriving an estimate of at least one fundamental frequency of the electrical signal, and stimulation pulse adjustment means for adjusting the stimulation pulses in accordance with the estimated fundamental frequency.

In a preferred embodiment of the invention, the feature extraction means comprises a plurality of fundamental frequency templates separating the electrical signal into a plurality of different frequency components, each template comprising a first template filter centred on a first frequency and one or more further template filters centred on harmonics of that first frequency, wherein the stimulation pulse adjustment means acts to compare output signals from the template filters in each template to determine a matching template passing maximum power compared to the remaining templates, the first frequency of the matching template being used by the stimulation pulse adjustment means as the estimated fundamental frequency.

The stimulation pulse adjustment means may selectively generate stimulation pulses during an electric stimulation period, the pulse adjustment means acting to convert the estimated fundamental frequency into the electric stimulation period using a specific conversion function.

In one embodiment, the specific conversion function may perform a first function of setting the longest interval between consecutive pulses in the temporal pattern during the electric stimulation period in accordance with the estimated fundamental frequency.

Additionally, or alternatively, the specific conversion function may perform a second function of setting the electric stimulation period in accordance with the estimated fundamental frequency.

The specific conversion function may vary between performing the first and second function.

The specific conversion function may preferentially perform the second function when the electrodes to be stimulated in the temporal pattern are physically proximate each other.

In the presence of two or more complex acoustic sounds, the feature extraction means may derive an estimate of multiple fundamental frequencies from the electrical signal and the specific conversion function may convert the multiple fundamental frequencies into a corresponding number of interleaved electric stimulation periods.

In another embodiment of the invention, the stimulation pulse adjustment means may modulate the amplitude of the stimulation pulses on all or a subset of activated electrodes at a modulation rate given by the estimated fundamental frequency.

The stimulation pulse adjustment means may further act to process the output signals from the template filters in the matching template to determine an estimate of one or more formants of the electrical signal.

The stimulation pulse adjustment means may modulate the amplitude of the stimulation pulses applied to one or more electrodes within the electrode array which correspond to the estimated one or more formants.

When the feature extraction means derives an estimate of multiple fundamental frequencies, each corresponding to a different complex acoustic sound, from the electrical signal, the stimulation pulse adjustment means may temporally segregate the amplitude modulation applied to the stimulation pulses for each different complex acoustic sound.

In a further embodiment, the stimulation pulse adjustment means may act to apply a temporal offset to the stimulation pulses applied to those electrodes within the electrode array which correspond to the estimated fundamental frequency or formants of the electrical signal with respect to the stimulation pulses applied to other electrodes in the electrode array.

The stimulation pulses may be applied simultaneously to those electrodes within the electrode array which correspond to the harmonic components of the complex sound, or formant frequencies of the acoustic signal.

Alternatively, the stimulation pulses applied to those electrodes within the electrode array which correspond to the harmonic components of the complex sound, or formant frequencies of the acoustic signal, may be temporally segregated from the stimulation pulses applied to the other electrodes in the electrode array.

Another aspect of the invention provides a bilateral auditory prosthesis apparatus including two auditory prosthesis devices as described hereabove.

The stimulation pulse adjustment means of a first of the auditory prosthesis devices may act to determine a matching template passing maximum power compared to the remaining templates in the first auditory prosthesis device, the first auditory prosthesis device further acting to determine the power passed by the corresponding template in the second auditory prosthesis device and, if less than the power passed by the matching template in the first auditory prosthesis device, adjusting the stimulation pulses in the first auditory prosthesis device in accordance with the estimated fundamental frequency.

In the presence of two complex acoustic sounds, the stimulation pulse adjustment means of the first auditory prosthesis device may act to determine to matching templates passing power maxima compared to the remaining templates in the first auditory prosthesis device, the stimulation pulse adjustment means of the first auditory prosthesis device adjusting the stimulation pulses in the first auditory prosthesis device in accordance with the estimated fundamental frequency corresponding to a first power maximum, and the stimulation pulse adjustment means of the second auditory prosthesis device adjusting the stimulation pulses in the second auditory prosthesis device in accordance with the estimated fundamental frequency corresponding to the second power maximum.

The stimulation pulse adjustment means of the first auditory prosthesis device may act to apply stimulation pulses to one or more electrodes in the first auditory prosthesis device which correspond to one or more formants of the complex acoustic sounds, and the stimulation pulse adjustment means of the second auditory prosthesis device may act to apply stimulation pulses, which are de-correlated with the stimulation pulses applied by the first auditory prosthesis device, to one or more electrodes in the second auditory prosthesis device which corresponds to the same one or more formants.

A further aspect of the invention provides a method of operating an auditory prosthesis device for selectively stimulating electrodes within an auditory prothesis electrode array, the method including:

converting a complex acoustic sound into an electrical signal, responsive to the electrical signal, generating a temporal pattern of stimulation pulses to selected electrodes within the electrode array, the stimulation pulses being applied to each electrode at an electrode stimulation rate, deriving an estimate of at least one fundamental frequency of the electrical signal, and adjusting the stimulation pulses in accordance with the estimated fundamental frequency.

The following description refers in more detail to the various features of the invention. To facilitate an understanding of the invention, reference is made in the description to the accompanying drawings where the auditory prosthesis device and method of its operation are illustrated in a preferred embodiment. It is to be understood however, that the invention is not limited to the preferred embodiment as shown in the drawings.

Existing auditory prosthesis devices include a microphone that converts sounds into electrical signals, and a sound processor responsive to the electrical signal from the microphone and selectively generating stimulation pulses for application to electrodes within an electrode array. In multi-channel cochlear implants, the electrode array is inserted in the cochlea so that different auditory nerve fibres can be simulated at different places in the cochlea. Typically, the electrode array includes 22 electrodes. Different electrodes in the electrode array are stimulated by the pulses from the sound processor depending upon the frequency of the electrical signal received from the microphone. The electrodes near the base of the cochlea are stimulated with electrical pulses derived from high frequency acoustic information, while electrodes near the apex are stimulated with electrical pulses derived from low frequency acoustic information. The sound processor acts to break the input signal into different frequency bands and selectively apply stimulation pulses to different electrodes within the electrode array based upon the signal in each of the frequency bands. Typically, the microphone and speech processor are worn by the patient, and stimulation pulses from the sound processor are transmitted to the electrode array by a transmitter/receiver pair.

Figure 1:
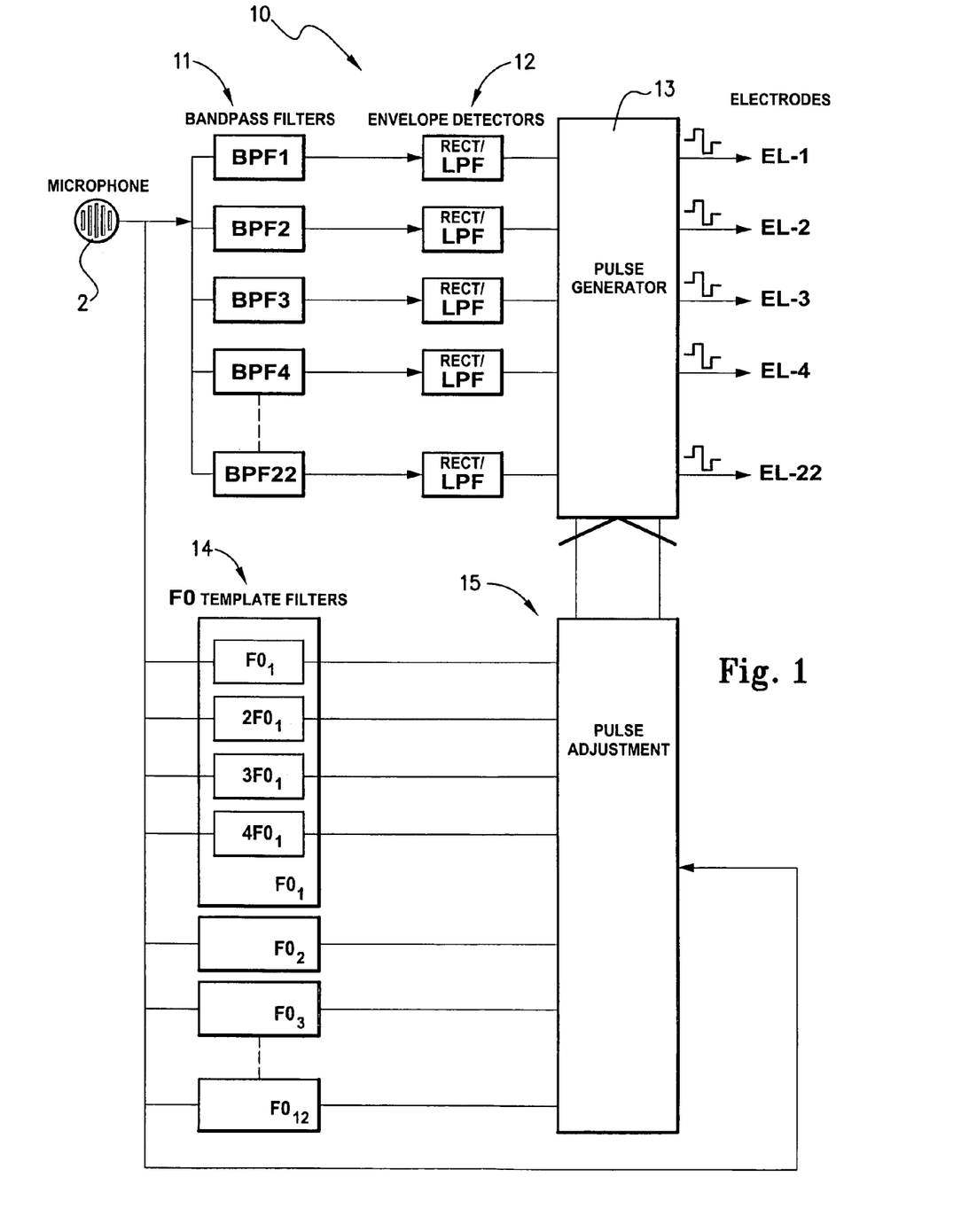
FIG. 1 is a schematic diagram showing various components of the sound processor of one embodiment of an auditory prosthesis device according to the present invention.

FIG. 1 shows a more detailed view of the various components of the sound processor. The sound processor 10 implements, in this embodiment, a Continuous Interleaved Sampling (CIS) sound processing strategy. The electrical signal from the microphone 2 is firstly pre-emphasised and then passed through a bank 11 of fixed overlapping bandpass filters. In this example, there are 22 bandpass filters (BFP1, BFP2 . . . BPF22), corresponding to the 22 electrodes within the electrode array 4. The envelopes of the filtered waveforms are then extracted by a bank 12 of full wave rectifiers and low-pass filters. The envelope outputs are then compressed and used by a pulse generator 13 to modulate biphasic pulses applied to the electrodes (El-1, El-2 . . . El-22) in the electrode array 4. In order to avoid channel interaction, trains of the biphasic pulses are delivered to the electrodes in a non-overlapping or non-simultaneous fashion, i.e., in a way such that only one electrode is stimulated at a time. The amplitude of the pulses is related to the amplitude of the envelopes detected by the envelope detectors.

Whilst the sound processing strategy used in this embodiment of the invention conforms to the CIS approach, it will be appreciated that other strategies that involve the passing of the electrical signal through a bank of fixed overlapping bandpass filters, the outputs of which determine the amplitude of the pulse applied to the corresponding electrode, may also be adopted. Examples of such strategies include the Advanced Combination Encoders (ACE) strategy, and the Spectral Peak (SPEAK) strategy. Alternatively, the amplitude of the stimulation pulses applied to each electrode may be determined from an acoustic loudness model together with an electrical loudness model, such as in the Specific Loudness (SpeL) strategy.

The sound processor 10 further comprises a bank 14 of fundamental frequency templates for deriving an estimate of at least one fundamental frequency of the electrical signal from the microphone 2. The bank 14 of fundamental frequency templates separates the electrical signal from the microphone 2 into different frequency components. Each fundamental frequency template comprises a first template filter centred on a first frequency within the frequency component and one or more further template filters centred on harmonics of that first frequency. In the example depicted in FIG. 2, the fundamental frequency template $F0_1$ includes a first template filter centred in practice on a fundamental frequency $F0_1$, and 3 template filters centred respectively on harmonics of that frequency, namely $2F0_1$, $3F0_1$ and $4F0_1$. In practice though, a fundamental frequency template may include any number of filters, and may typically include ten filters.

Similarly, the fundamental frequency templates $F0_2$, $F0_3$ . . . $F0_{12}$ shown in FIG. 1 each include a first template filter centred on a fundamental frequency and a series of filters centred respectively on harmonics of that frequency.

The frequency spacing between the fundamental frequency on which the first template filter in each template is centred will depend upon the ability of the cochlea implantee to distinguish sounds. Typically, the values of the fundamental frequencies detected by the templates may be derived from the standard musical scale. In one embodiment, the fundamental frequencies may be spaced from each other by a semi-tone.

Each fundamental frequency template defines an ordered list of frequencies. Each frequency specifies the lower or upper sound of a different fundamental frequency and its associated harmonics that may potentially be present in the signal detected by the microphone 2. The upper and lower sounds may be spaced by a half semi-tone on either side of the centre frequency for each harmonic. For example, the fundamental frequency template for the note "A" would define the upper and lower bounds of the first template filter at 213.7 Hz and 226.4 Hz (220 Hz+0.5 semi-tone), and the upper and lower bounds of the subsequent template filters at 427.5 Hz and 452.9 Hz, 641.2 Hz and 679.3 Hz, 854.9 Hz and 905.8 Hz, and so on.

The output signals from the template filters within each fundamental frequency template filter are provided to a stimulation pulse adjustment device 15.

Figure 2:
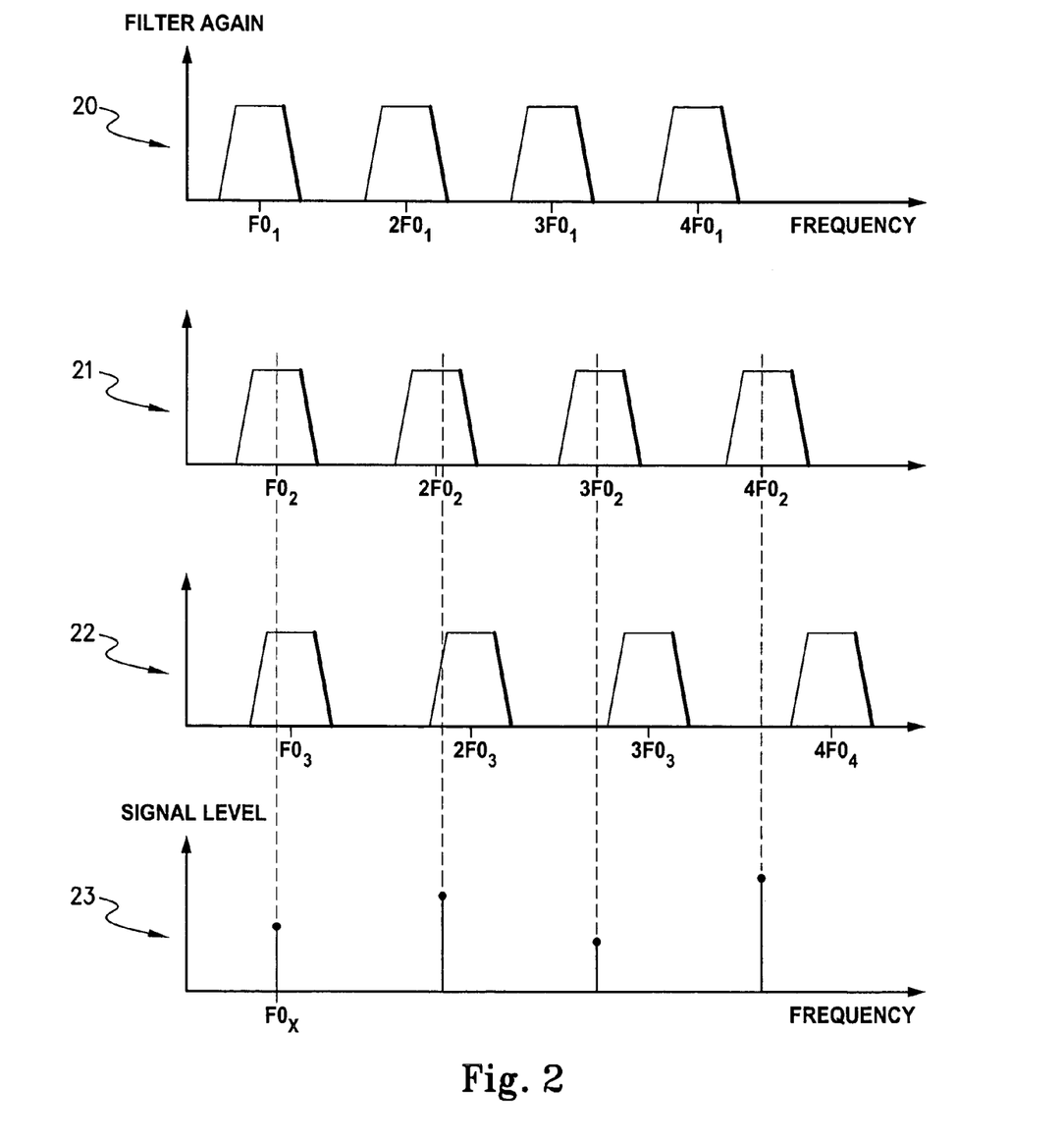
FIG. 2 is a graphical representation of the pass bands of the first four template filters within each of three fundamental frequency templates forming part of the sound processor of FIG. 1, and a harmonic input spectrum to be processed using these templates.

FIG. 2 illustrates the pass bands 20, 21 and 22 of the first four template filters in each of the first three fundamental frequency templates $F0_1$, $F0_2$, and $F0_3$ shown in FIG. 1. Input signal power that is passed by the template filters with the template $F0_1$ for example, is assumed to arise from a harmonic signal with a fundamental frequency approximately equal to $F0_1$, whereas the input power that is not passed by the filters within this template is assumed to arise from noise.

An example of a harmonic input spectrum 23 of a signal from the microphone 2 to be processed by a set of templates including template filters having the pass bands shown in FIG. 2 is also depicted. The input spectrum has a fundamental frequency of $F0_x$. The lowest four harmonics of $F0_x$ are shown, starting at $F0_x$. Although the magnitudes of the harmonic components vary, it can be seen from this figure that the largest amount of power contained in the spectrum would be passed by the template having filters centred on $F0_2$ and its harmonic components, when compared to the amount of power passed by the other templates. Accordingly, the fundamental frequency $F0_2$ can be taken to be an estimate of the value of the fundamental frequency $F0_x$.

The pulse adjustment device 15 compares the signals from the filters in each of the templates in the bank 14 to determine the template passing the maximum power compared to the other templates. The first frequency upon which the first filter within that template filter is centred is taken to be an estimate of the fundamental frequency of the signal from the microphone 2.

Furthermore, the output signals of the filters within the template passing the maximum power can be processed by the pulse adjustment device 15 to extract local spectral peaks. In effect, the filters within that template act to sample the complex harmonic signal detected by the microphone 2, and further processing of this sampled signal can provide an estimate of the formant frequencies in the case of voiced speech or a similar type of sound.

To better determine the template(s) passing the maximum power compared to the other templates, a weighting function may be applied by the pulse adjustment device 15 to the outputs, of all filters in the templates. For example, a weighting may be applied to increase the value of the output signal strength of those templates centred on a fundamental frequency in the mid-range of human hearing. For each template, the outputs of the filters are amplified or attenuated according to their centre frequencies. The range of centre frequencies over which an appropriate waiting function is applied may typically be between 500 to 1500 Hz.

It is to be understood that in other embodiments of the invention, other techniques can be used to provide a real-time estimate of the fundamental frequency of a complex harmonic signal detected by the microphone 2. The choice of an F0 analysis technique may be made with respect to the nature of the input signal, the acoustic conditions in which the system will be used and the analysis output errors that are acceptable and those that are not. The techniques include time domain techniques, frequency domain techniques, hybrid time and frequency domain techniques and direct measurement of larynx activity.

Time domain f0 estimation techniques exploit the fact that the waveform of a periodic sound repeats, and they detect features which occur once per cycle during voiced sounds, such as the major positive (or negative) peak, positive- (or negative-) going zero crossings, the slope changes associated with major peaks or any readily identifiable feature on the waveform which can be identified as occurring once per cycle.

Frequency domain f0 estimation techniques take advantage of the fact that the frequency spectrum of a periodic signal has a series of regularly spaced peaks, or 'harmonics', and a non-periodic signal has a continuous spectrum with no regularly spaced peaks. F0 estimation is typically based on finding and tracking either: (a) the f0 component (first harmonic) itself; or (b) the frequency difference between any two adjacent harmonics, which is equal to f0; or (c) the f0 which best 'fits' all the harmonics present.

Hybrid techniques make use of a combination of time and frequency domain features such that some merits of one domain might override some drawback of the other domain. Direct measurement of larynx activity can be based on the use of a throat microphone, or electrical impedance measurements systems such as the electrolaryngograph or electroglottograph.

An advantage of the technique for identifying the fundamental frequency of the electrical signal described in relation to FIG. 1 is that, as stated above, it also identifies the frequency components of the complex harmonic signal.

A further advantage of this technique is that it enables the identification of two concurrent complex sounds. In this case, there with be maxima at the output of two fundamental frequency templates within the bank 14, each maxima corresponding to an estimate of a separate fundamental frequency.

Furthermore, the outputs of the filters in these two templates will specify which spectral components belong to each fundamental frequency.

A third advantage is that the signal to noise ratio can be estimated by comparing the total power at the output of the matching fundamental frequency template with the total power of those components of the signal that do not coincide with any of the filters in the matching fundamental frequency template. Such a signal to noise ratio estimate is an indication of the reliability of the estimated fundamental frequency value(s).

To that effect, the stimulation pulse adjustment device 15 additionally detects the level of the total overall signal captured by the microphone 2 without being firstly filtered by the bank 14 of templates. The total overall signal is a combination of the complex harmonic signals (if any) and noise that is detected by the microphone 2. The total overall signal strength may be compared by the pulse adjustment device 15 to the signal strength at the outputs of the matching fundamental frequency templates to determine either a complex harmonic signal-to-noise ratio or a complex harmonic signal-to-overall signal ratio. If one or both of these ratios is below a predetermined threshold value, no pulse adjustment may be applied.

Alternatively, no pulse adjustment may be applied if the pulse adjustment device 15 determines that the overall signal strength is below a predetermined threshold value and that the estimate of the fundamental frequency of the complex harmonic signal is likely to be unreliable.

If none of the outputs of the templates are determined by the pulse adjustment device 15 are determined to have a power greater than any of the others (i.e. a high level signal is detected at all templates), no pulse adjustment may also be applied.

Rather than simply applying no pulse adjustment in the above-described scenarios, the pulse adjustment device 15 may alternately set the stimulation rate of the pulses applied by the pulse generator 13 to either a fixed high rate of stimulation or a random stimulation rate.

The estimations of the fundamental frequency (or fundamental frequencies) can be used by the pulse adjustment device 15 to modify the "usual" output of the pulse generator 13 in a variety of ways. Each of these adjustments allows the main components of the complex sound to be perceptually grouped by the cochlear implantee, and also allows the implantee to better perceive the fundamental frequency pitch.

Figure 3:
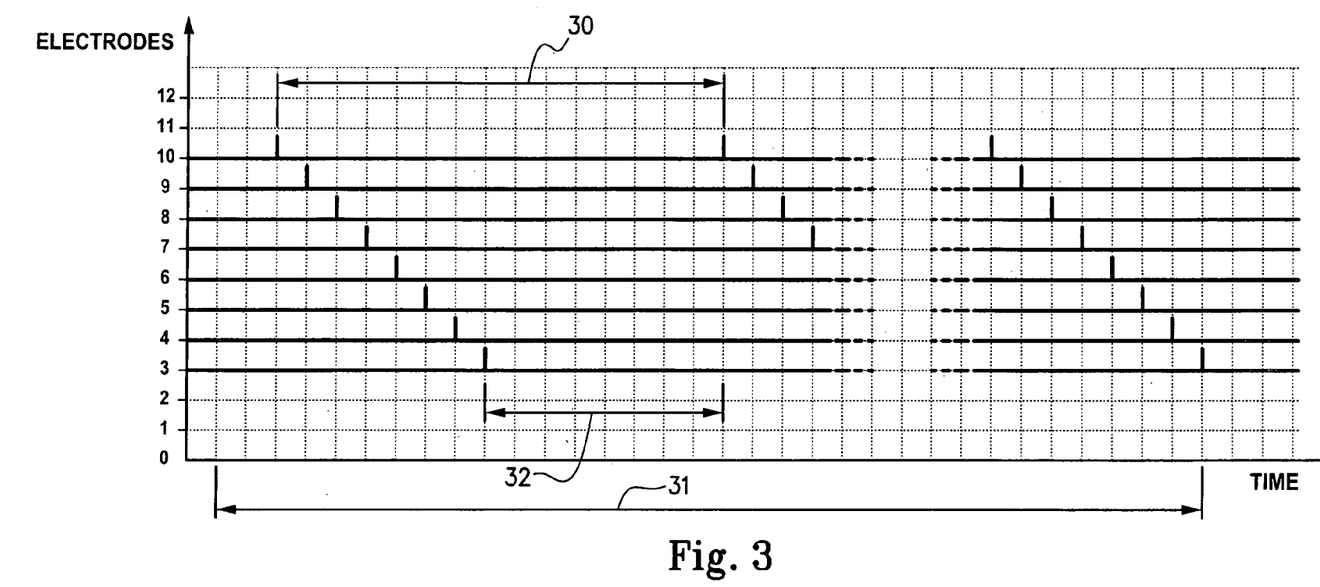
FIG. 3 is a graphic representation of a temporal pattern of electrical stimulation pulses applied to an electrode array in an auditory prosthesis device.

In a first technique, the stimulation pulse adjustment means applies information derived from the estimated fundamental frequency to the temporal pattern of pulses generated by the pulse generator 13. FIG. 3 shows one example of such a temporal patter of pulses applied to electrodes within an electrode array of a cochlea implant. In this example, pulses are delivered to the electrodes in a non-overlapping fashion so that only one electrode is stimulated at a time. Each electrode is stimulated at an electrode stimulation period 30 determined by the interval between consecutive pulses applied to a same electrode. The temporal pattern of pulses shown in FIG. 3 is applied to selected electrodes within an electrode array of cochlea implant during an electric stimulation period, or control period, referenced 31. The longest interval between consecutive pulses in the temporal pattern shown in FIG. 3 is referenced 32.

In its simplest form, the stimulation pulse adjustment means can set the electrode stimulation rate to be equal to the estimated fundamental frequency. However, psychophysical research has indicated that, where multiple pulses are applied to an electrode in an electrode stimulation period, the pitch perceived is related to the longest interval in the pattern, rather than the stimulation period. Furthermore, it has been shown that stimulation on nearby electrodes is perceptually amalgamated to form an overall pitch perception. Accordingly, the specific conversion function used by the pulse adjustment device 15, in a first embodiment, sets the longest interval between consecutive pulses in the temporal pattern during the electric stimulation period in accordance with the estimated fundamental frequency. In this way, an appropriate pitch verses fundamental frequency conversion is produced for implantees. The principle is applicable when multiple pulses are present in the temporal electrical stimulation pattern for each electric stimulation period.

For example, it is possible to run through each group of active electrodes in a usual ACE or CIS scheme more than once within each electric stimulation period, at least for speech sources or other low values of fundamental frequency. With existing, fast cochlea stimulators, eight selected electrodes may typically be activated on each of, for example, four stimulation cycles with a time interval that is shorter than half the period of a typical speech fundamental frequency. Thus, even if stimulation gaps of length equal to the period of the fundamental frequency are incorporated into the electric stimulation period, an overall high rate of stimulation can be achieved.

The specific conversion function may also be used to set the electric stimulation rate at which pulses are applied to individual electrodes in accordance with the estimated fundamental frequency.

The specific conversion function may also vary between setting the longest inter-pulse interval to correspond with the estimated fundamental frequency, and setting the electrode stimulation rate to correspond with the estimated fundamental frequency. The specific conversion function may vary between the two different conversions applied to the stimulation pulses in a gradual manner. The specific conversion function may preferentially perform the setting of the longest inter-pulse interval to correspond to the estimated fundamental frequency particularly where the electrodes to be stimulated in the temporal pattern are physically proximate to each other.

Where the bank 14 of templates derives an estimate of multiple fundamental frequencies from the electrical signal, thereby indicating the presence of multiple complex sounds, the specific conversion function converts the multiple fundamental frequencies into a corresponding number of interleaved electric stimulation periods. It may be that only one or two electrode stimulation cycles are p resent for each electric stimulation period.

Another technique that may be implemented by use of the pulse adjustment device 15 involves the imposition of an in-phase fundamental frequency amplitude modulation to the output of the pulse generator 13. In its simplest form, the amplitude of every activated electrode can be modulated by the pulse adjustment device 15 in accordance with the estimated fundamental frequency.

A more sophisticated strategy may be to modulate the amplitude of the stimulation pulses applied to one or more electrodes within the electrode array which correspond to the estimated one or more formants. As described previously, the output signals of the template filters in the matching fundamental frequency template can be processed to determine an estimate of one or more formants of the complex acoustic sound.

The concurrent and in-phase amplitude modulation of the stimulation pulses applied to the formant electrodes improves perception of the fundamental frequency pitch of the complex sound. Moreover, the "marking" of the formants with an amplitude modulation corresponding to the fundamental frequency of the complex sound allows these important components to be perceptually grouped as belonging together, and segregated from any concurrent sounds or noise.

Keeping the modulation pattern smooth as the fundamental frequency changes can be achieved, for example, by using a modulation weighting function in which the phase of the function varies smoothly. That is, the phase of the weighting for the next pulse can be an increment of the previous phase, the size of the increment being determined by the next fundamental frequency estimate and the time elapsed.

The above-described techniques can be used in the case of two or more concurrent complex sounds. Where the bank 14 of templates derives an estimate of two fundamental frequencies, each corresponding to a different complex acoustic sound, there will be two templates that provide significant output signals, or power maxima. In this case, there will be two fundamental frequencies each with different formant estimates provided by the output of two matching templates within the bank 14 of fundamental frequency templates. Thus, there may be four electrodes which correspond to the estimated formants, which are marked with appropriate amplitude modulation patterns. The different modulation rates on the two different pairs of electrodes will enable the formants to be paired to make correct vowels and for the two vowels, or musical sounds, to be heard as perceptually separate.

An alternative arrangement involves the stimulation pulse adjustment device applying a temporal segregation of the amplitude modulation applied to the stimulation pulses for each different complex acoustic sound. For example, a temporal offset may be applied to the stimulation pulses applied to those electrodes within the electrode array which correspond to the harmonic components or formant frequencies of the acoustic signal, with respect to the simulation pulses applied to other electrodes in the electrode array. The stimulation pulses may be applied simultaneously to those electrodes within the electrode array which correspond to the harmonic components or formant frequencies of the acoustic signal.

Alternatively, the stimulation pulses applied to those electrodes within the electrode array which correspond to the harmonic components or formant frequencies of the acoustic signal may be temporally segregated from the stimulation pulses applied to other electrodes in the electrode array. For example, the group of electrodes corresponding to the harmonic components or formant frequencies of the acoustic signal may be activated in close succession, following by a temporal gap before activation of any additional electrodes.

Figure 4:
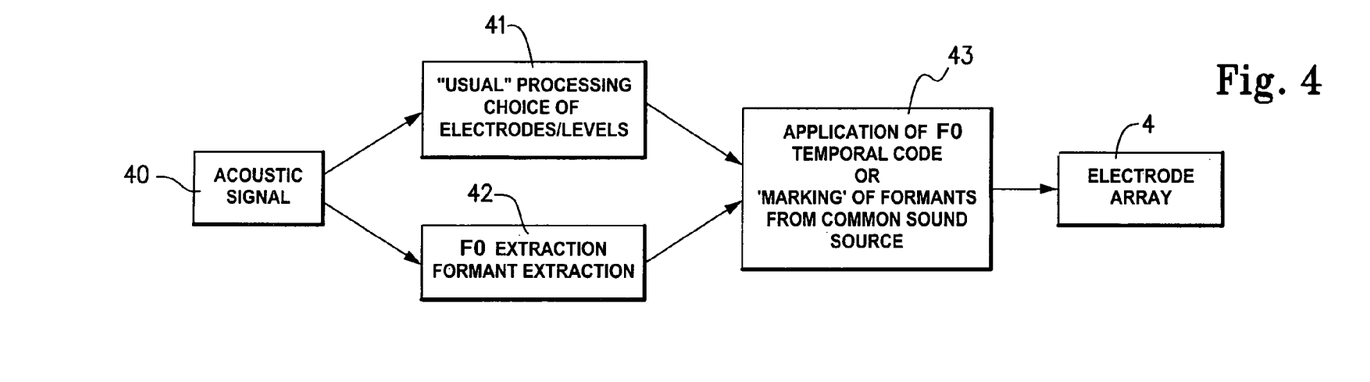
FIG. 4 is a flow chart showing schematically the series of functional operations performed by the sound processor of FIG. 1.

As seen in FIG. 4, each of the above described variants all have a common initial processing step in which an acoustic signal 40 is processed in a conventional manner, in a first step 41, to determine an electrical level to be applied to each of the electrodes in the electrode array 4. In concurrent step 42, the fundamental frequency of the acoustic signal 40 is extracted. Preferably, the formants of the complex harmonics signal are also extracted together with the harmonic components of the signal. At step 43, the information extracted at step 32 is used to adjust the simulation pulses conventionally produced by existing sound processing techniques.

Figure 5:
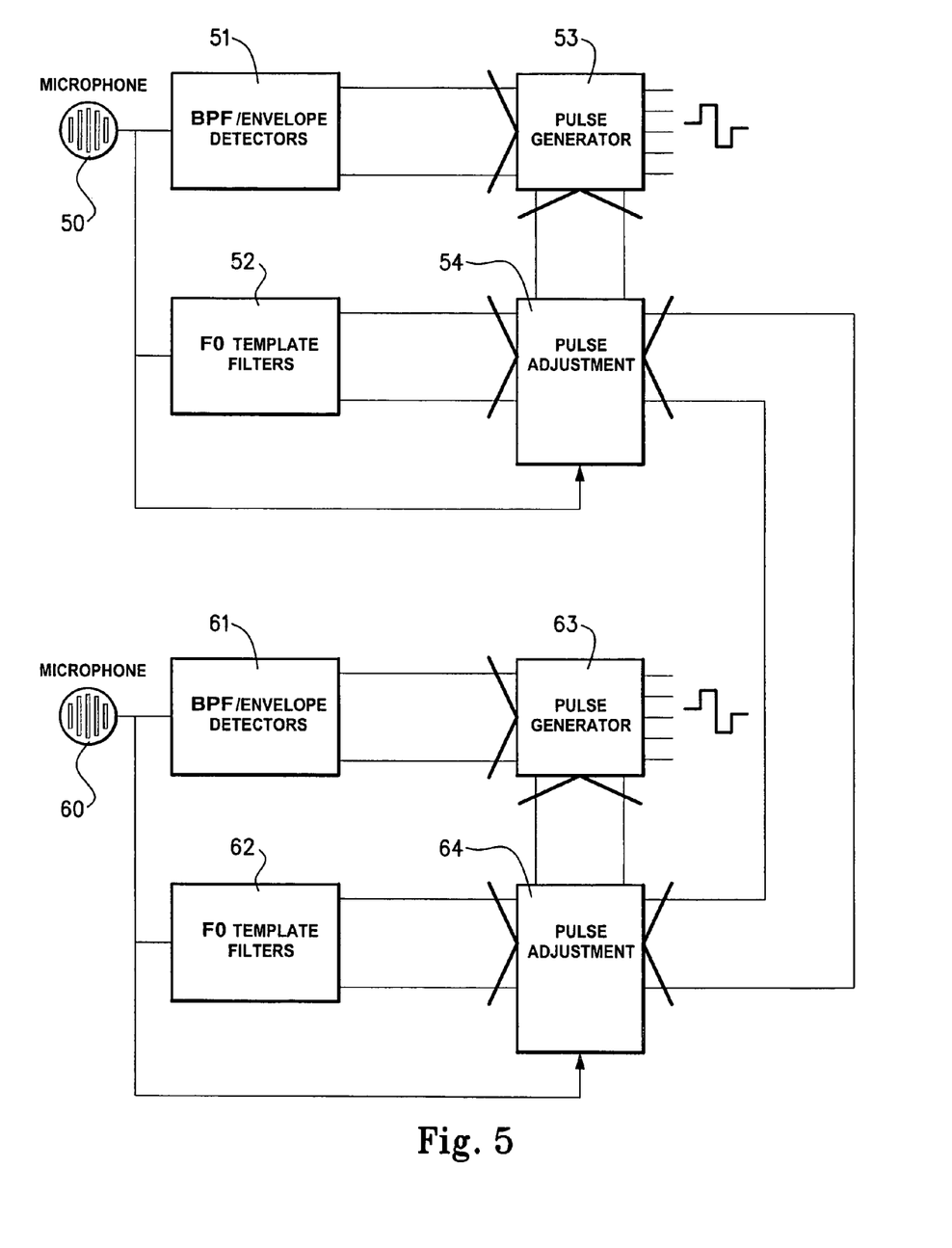
FIG. 5 is a schematic diagram of a part of bilateral auditory prosthesis apparatus including two sound processors.

The above described techniques can also be adapted to an bilateral auditory prosthesis apparatus in which a separate auditory prosthesis device is provided for each ear of a user. FIG. 5 illustrates one example of such a bilateral apparatus. A first microphone 50 converts acoustic signals into an electrical signal provided to the input of a bank 51 of bandpass filters and envelope detectors, and also to a bank 52 of spectral template filters. A pulse generator 53 selectively generates stimulation pulses to electrodes within a first electrode array implanted in a first ear of a user. Information relating to the fundamental frequency of the electrical signal is derived from the output of the filters in the bank 52 by a pulse adjustment device 54. The pulse adjustment device 54 acts to modify the stimulation pulses generated by the pulse generator 53 in the manner described in relation to FIG. 3.

Similarly, a second microphone 60 is provided to convert an acoustic signal into an electrical signal provided to the input of a bank 61 of bandpass filters and envelope detectors and to a bank 62 of spectral template filters. A pulse generator 63 acts to selectively generate stimulation pulses to electrodes within a second electrode array implanted in the other each of a user. Information relating to the fundamental frequency of the electric signal, provided by the bank 62 of template filters, is used by a pulse adjustment device 64 to modify the stimulation pulses generated by the pulse generator 63. In its simplest form, the auditory prosthesis devices operate independently and separately process complex sounds detected by their respective microphones. However, in the example shown in FIG. 5, processing carried out in one auditory prosthesis device impacts the processing carried out in the other auditory prosthesis device.

The above described information relating to the fundamental frequency of the complex signal detected by the microphones 50 and 60 determined by the pulse adjustment devices 54 and 64 in FIG. 5, are shared between these two devices by a data bus.

An important feature of any bilateral fitting is that the frequency to electrode allocation in each ear should be arranged so that particular frequency bands are allocated to pitch matched electrodes in each ear. In the example shown in FIG. 4, each of the microphones 50 and 60 are arranged on opposite sides of the head, and separate processing of the signals for each microphone is provided. In this case, the pulse adjustment devices 54 and 64 each act to determine a matching template passing the maximum power compared to the remaining templates. Each of the pulse adjustment devices 54 and 64 then determines the power passed by the corresponding template in the other auditory prosthesis device.

If the power passed by this corresponding template is less than the power passed by the matching template with which each pulse adjusting device is associated, the stimulation pulse adjustment device will adjust the simulation pulses as described hereabove. In this way, modification of the stimulation pulses need only occur on the side determined to have the larger output signal, this being the side where the dominant sound source is located. The template passing the maximum power in each auditory prosthesis device is used to "mark" the electrodes corresponding to the features on that side (i.e. with fundamental frequency modulations or temporal offsets) or alternatively to create fundamental frequency based control intervals, provided the power passed by the corresponding template in the other auditory prosthesis device is less than the power passed by that matching template.

In the case of two concurrent complex sounds being present, if they are spatially separated, separate modifications to the stimulation pulses on each side can be made. For example, when in the presence of two complex acoustic sounds, the pulse adjustment device 54 determines that there are two matching templates passing power maxima compared to the remaining templates in the bank 52 of templates, the pulse adjustment device 54 can adjust the stimulation pulses generated by the pulse generator 53 in accordance with the estimated fundamental frequency corresponding to the first power maximum, whilst the pulse adjustment device 64 adjusts the stimulation pulses generated by the pulse generator 63 in accordance with the estimated fundamental frequency corresponding to the second power maximum.

In addition, or alternatively to the above bilateral scheme, stimulation pulses applied to electrodes corresponding to one or more formants of a complex acoustic sound by one of the auditory prosthesis devices can be de-correlated with stimulation pulses applied by the other of the auditory prosthesis devices to the corresponding electrodes in that other device. In other words, when the pulse adjustment device 54 in the example shown in FIG. 5, adjusts pulses applied to one or more electrodes which correspond to one or more formants of a complex acoustic sound, the pulse adjustment device 64 acts to apply stimulation pulses that are de-correlated with the stimulation pulses adjusted by the pulse adjustment device 54, to one or more electrodes in the other auditory prosthesis device which correspond to the same one or more formants. The de-correlation may be effected by applying a different electrode stimulation rate to electrodes corresponding to the same formants in each auditory prosthesis device. This can be achieved in practice by incrementing the position of these electrodes in the order of electrode activation in the temporal pattern of pulses applied to the electrode array each electric stimulation period.

It is to be understood that various modifications and/or additions may be made to the above described auditory prosthesis device and method for operating the auditory prosthesis device without departing from the spirit or ambit of the present invention.

The invention claimed is:

1. An auditory prosthesis device for selectively stimulating electrodes within an auditory prosthesis electrode array, comprising:
   a transducer for converting a complex acoustic sound into an electrical signal,
   signal processing means responsive to an electrical signal and generating a temporal pattern of stimulation pulses to selected electrodes within the electrode array, the stimulation pulses being applied to each electrode at an electrode stimulation rate,
   feature extraction means for deriving an estimate of at least one fundamental frequency of the electrical signal, and
   stimulation pulse adjustment means for adjusting the stimulation pulses in accordance with the estimated fundamental frequency.

2. An auditory prosthesis device according to claim 1, wherein;
   the feature extraction means comprises a plurality of fundamental frequency templates separating the electrical signal into a plurality of different frequency components, each template comprising a first template filter centred on a first frequency and one or more further template filters centred on harmonics of that first frequency, and wherein
   the stimulation pulse adjustment means act to compare output signals from the template filters in each template to determine a matching template passing maximum power compared to the remaining templates, the first frequency of the matching template being used by the stimulation pulse adjustment means as the estimated fundamental frequency.

3. An auditory prosthesis device according to claim 2, wherein the stimulation pulse adjustment means selectively generates stimulation pulses during an electric stimulation period, the pulse adjustment means acting to convert the estimated fundamental frequency into the electric stimulation period using a specific conversion function.

4. An auditory prosthesis device according to claim 3, wherein the specific conversion function performs a first function of setting the longest interval between consecutive pulses in the temporal pattern during the electric stimulation period in accordance with the estimated fundamental frequency.

5. An auditory prosthesis device according to claim 4, wherein the specific conversion function performs a second function of setting the electric stimulation period in accordance with the estimated fundamental frequency.

6. An auditory prosthesis device according to claims 4 or 5, wherein the specific conversion function varies between performing the first and second function.

7. An auditory prosthesis device according to claims 4 or 5, wherein the specific conversion function preferentially performs the second function when the electrodes to be stimulated in the temporal pattern are physically proximate each other.

8. An auditory prosthesis device according to claim 2, wherein, in the presence of two or more complex acoustic sounds, the feature extraction means derive an estimate of multiple fundamental frequencies from the electrical signal and the specific conversion function converts the multiple fundamental frequencies into a corresponding number of interleaved electric stimulation periods.

9. An auditory prosthesis device according to claim 1, wherein the stimulation pulse adjustment means modulate the amplitude of the stimulation pulses applied to all or a subset of activated electrodes with a modulation rate corresponding to the estimated fundamental frequency.

10. An auditory prosthesis device according to claim 1, wherein the stimulation pulse adjustment means to processes the output signals from the template filters in the matching template to determine an estimate of one or more formants of the electrical signal.

11. An auditory prosthesis device according to claim 1, wherein the stimulation pulse adjustment means modulate the amplitude of the stimulation pulses applied to one or more electrodes within the electrode array which correspond to the estimated one or more formants.

12. An auditory prosthesis device according to claim 1, wherein, when the feature extraction means derives an estimate of multiple fundamental frequencies, each corresponding to a different complex acoustic sound, from the electrical signal, the stimulation pulse adjustment means temporally segregate the amplitude modulation applied to the stimulation pulses for each different complex acoustic sound.

13. An auditory prosthesis device according to claim 1, wherein the stimulation pulse adjustment means act to apply a temporal offset to the stimulation pulses applied to those electrodes within the electrode array which correspond to harmonic components or formant frequencies of the acoustic signal with respect to the stimulation pulses applied to other electrodes in the electrode array.

14. An auditory prosthesis device according to claim 13, wherein the stimulation pulses are applied simultaneously to those electrodes within the electrode array which correspond to harmonic components or formant frequencies of the acoustic signal.

15. An auditory prosthesis device according to claims 1, wherein the stimulation pulses applied to those electrodes within the electrode array which correspond to harmonic components or formant frequencies of the acoustic signal are temporally segregated from the stimulation pulses applied to the other electrodes in the electrode array.

16. A bilateral auditory prosthesis apparatus including two auditory prosthesis devices according to claim 1.

17. A bilateral auditory prosthesis apparatus according to claim 16, wherein the stimulation pulse adjustment means of a first of the auditory prosthesis devices act to determine a matching template passing maximum power compared to the remaining templates in the first auditory prosthesis device, the first auditory prosthesis device further acting to determine the power passed by the corresponding template in the second auditory prosthesis device and, if less than the power passed by the matching template in the first auditory prosthesis device, adjusting the stimulation pulses in the first auditory prosthesis device in accordance with the estimated fundamental frequency.

18. A bilateral auditory prosthesis apparatus according to either one of claims 16 or 17, wherein, in the presence of two complex acoustic sounds, the stimulation pulse adjustment means of the first auditory prosthesis device act to determine to matching templates passing power maxima compared to the remaining templates in the first auditory prosthesis device, the stimulation pulse adjustment means of the first auditory prosthesis device adjusting the stimulation pulses in the first auditory prosthesis device in accordance with the estimated fundamental frequency corresponding to a first power maximum, and the stimulation pulse adjustment means of the second auditory prosthesis device adjusting the stimulation pulses in the second auditory prosthesis device in accordance with the estimated fundamental frequency corresponding to the second power maximum.

19. A bilateral auditory prosthesis apparatus according to claim 16, wherein the stimulation pulse adjustment means of the first auditory prosthesis device act to apply stimulation pulses to one or more electrodes in the first auditory prosthesis device which correspond to one or more formants of the complex acoustic sounds, and the stimulation pulse adjustment means of the second auditory prosthesis device act to apply stimulation pulses, which are de-correlated with the stimulation pulses applied by the first auditory prosthesis device, to one or more electrodes in the second auditory prosthesis device which corresponds to the same one or more formants.

20. A method of operating an auditory prosthesis device for selectively stimulating electrodes within an auditory prothesis electrode array, the method including:
converting a complex acoustic sound into an electrical signal;
responsive to the electrical signal, generating a temporal pattern of stimulation pulses to selected electrodes within the electrode array, the stimulation pulses being applied to each electrode at an electrode stimulation rate;
deriving an estimate of at least one fundamental frequency of the electrical signal; and
adjusting the stimulation pulses in accordance with the estimated fundamental frequency.

21. A method according to claim 20, wherein the feature extraction means comprising a plurality of fundamental frequency templates separating the electrical signal into a plurality of different frequency components, each template comprising a first template filter centred on a first frequency and one or more further template filters centred on harmonics of that first frequency, and wherein the step of adjusting the stimulation pulses includes:
comparing output signals from the template filters in each template to determine a matching template passing maximum power compared to the remaining templates, the first frequency of the matching template being used as the estimated fundamental frequency.

22. A method according to claim 21, wherein the step of adjusting the stimulation pulses further includes:
selectively generating stimulation pulses during an electric stimulation period; and
converting the estimated fundamental frequency into the electric stimulation period using a specific conversion function.

23. A method according to claim 22, wherein the specific conversion function performs a first function of setting the longest interval between consecutive pulses in the temporal pattern during the electric stimulation period in accordance with the estimated fundamental frequency.

24. A method according to claim 22, wherein the specific conversion function performs a second function of setting the electric stimulation period in accordance with the estimated fundamental frequency.

25. A method according to claims 23 or 24, wherein the specific conversion function varies between performing the first and second function.

26. A method according to claims 23 or 24, wherein the specific conversion function preferentially performs the second function when the electrodes to be stimulated in the temporal pattern are physically proximate each other.

27. A method according to claim 22, wherein, in the presence of two or more complex acoustic sounds, the step of deriving an estimate of at least one fundamental frequency of the electrical signal includes:
deriving an estimate of multiple fundamental frequencies from the electrical signal;
using the specific conversion function to convert the multiple fundamental frequencies into a corresponding number of interleaved electric stimulation periods.

28. A method according to claim 20, wherein the step of adjusting the stimulation pulses includes:
modulating the amplitude of the stimulation pulses applied to all or a subset of activated electrodes with a modulation rate corresponding to the estimated fundamental frequency.

29. A method according to claim 20, wherein the step of adjusting the stimulation pulses includes:
processing the output signals from the template filters in the matching template to determine an estimate of one or more formants of the electrical signal.

30. A method according to claim 20, wherein the step of adjusting the stimulation pulses includes:
modulating the amplitude of the stimulation pulses applied to one or more electrodes within the electrode array which correspond to the estimated one or more formants.

31. A method according to claim 20, wherein, when the step of deriving an estimate of at least one fundamental frequency of the electrical signal includes deriving an estimate of multiple fundamental frequencies, each corresponding to a different complex acoustic sound, from the electrical signal, the step of adjusting the stimulation pulses includes:
temporally segregating the amplitude modulation applied to the stimulation pulses for each different complex acoustic sound.

32. A method according to claim 20, wherein the step of adjusting the stimulation pulses includes:
applying a temporal offset to the stimulation pulses applied to those electrodes within the electrode array which correspond to harmonic components or formant frequencies of the acoustic signal with respect to the stimulation pulses applied to other electrodes in the electrode array.

33. A method according to claim 32, wherein the step of adjusting the stimulation pulses further includes:
simultaneously applying stimulation pulses to those electrodes within the electrode array which correspond to the estimated fundamental frequency or formants of the electrical signal.

34. An auditory prosthesis device according to claims 20, wherein the step of adjusting the stimulation pulses further includes:
temporally segregating the stimulation pulses applied to those electrodes within the electrode array which correspond to harmonic components or formant frequencies of the acoustic signal from the stimulation pulses applied to the other electrodes in the electrode array.

35. A method of operating a bilateral auditory prosthesis apparatus including two auditory prosthesis devices according to claims 1, the method including operating each auditory prosthesis device according to claim 20.

36. A method of operating a bilateral auditory prosthesis apparatus according to claim 35, wherein the step of adjusting the stimulation pulses of a first of the auditory prosthesis devices further includes:
determining a matching template passing maximum power compared to the remaining templates in the first auditory prosthesis device;
the method further including:
determining the power passed by the corresponding template in the second auditory prosthesis device and, if less than the power passed by the matching template in the first auditory prosthesis device;
the step of adjusting the stimulation pulses of a first of the auditory prosthesis devices further including:
adjusting the stimulation pulses in the first auditory prosthesis device in accordance with the estimated fundamental frequency.

37. A method of operating a bilateral auditory prosthesis apparatus according to either one of claims 35 or 36, wherein, in the presence of two complex acoustic sounds, the step of adjusting the stimulation pulses of a first of the auditory prosthesis devices includes:
determining matching templates passing power maxima compared to the remaining templates in the first auditory prosthesis device;
adjusting the stimulation pulses in the first auditory prosthesis device in accordance with the estimated fundamental frequency corresponding to a first power maximum;
the step of adjusting the stimulation pulses of a second of the auditory prosthesis devices including:
adjusting the stimulation pulses in the second auditory prosthesis device in accordance with the estimated fundamental frequency corresponding to the second power maximum.

38. A method of operating a bilateral auditory prosthesis apparatus according to claim 35, wherein the step of adjusting the stimulation pulses of a first of the auditory prosthesis devices further includes:
applying stimulation pulses to one or more electrodes in the, first auditory prosthesis device which correspond to one or more formants of the complex acoustic sounds;
the step of adjusting the stimulation pulses of a second of the auditory prosthesis devices further including:
applying stimulation pulses, which are de-correlated with the stimulation pulses applied by the first auditory prosthesis device, to one or more electrodes in the second auditory prosthesis device which corresponds to the same one or more formants.

* * * * *